United States Patent [19]

Jenck et al.

[11] Patent Number: 5,077,433

[45] Date of Patent: Dec. 31, 1991

[54] PREPARATION OF HEXENE-1,6-DIOIC ACIDS

[75] Inventors: Jean Jenck, Chassieu; Philippe Denis, Decines; Philippe Kalck, Castanet Tolosane; Helene Deweerdt, Lyons, all of France

[73] Assignee: Rhone-Poulenc Chimie, Courbevoie, France

[21] Appl. No.: 516,743

[22] Filed: Apr. 30, 1990

[30] Foreign Application Priority Data

Apr. 28, 1989 [FR] France ................................ 89 06018

[51] Int. Cl.$^5$ ............................................. C07C 51/12
[52] U.S. Cl. ..................................... 562/517; 560/204; 562/595
[58] Field of Search .................. 562/517, 595; 560/204

[56] References Cited

U.S. PATENT DOCUMENTS 4,259,519 3/1981 Stille ..................................... 560/193

*Primary Examiner*—José G. Dees
*Assistant Examiner*—Vera C. Clarke
*Attorney, Agent, or Firm*—Burns, Doane, Swecker & Mathis

[57] ABSTRACT

The hexene-1,6-dioic acids, e.g., hex-3-ene-1,6-dioic acid, are prepared by reacting carbon monoxide and water with at least one diacyloxylated butene, in the presence of a catalytically effective amount of palladium and at least one quaternary onium chloride of one of the Group VB elements nitrogen or phosphorus, such element being tetracoordinated via carbon atoms and with the proviso that such nitrogen atom may be coordinated to two pentavalent phosphorus atoms.

18 Claims, No Drawings

PREPARATION OF HEXENE-1,6-DIOIC ACIDS

BACKGROUND OF THE INVENTION

1. Field of the Invention

The present invention relates to the preparation of hexene-1,6-dioic acids, in particular hex-3-ene-1,6-dioic acid.

2. Description of the Prior Art

It is known to this art that hex-3-ene-1,6-dioic acid is readily hydrogenated into adipic acid.

Adipic acid, one of the basic starting materials for nylon 66, is currently produced in vast amounts, and, for this reason alone, any novel process providing access to such diacid and/or derivative thereof would be of significant interest to this art.

Continuing, U.S. Pat. No. 4,611,082 indicates that it is virtually impossible to carbonylate a solution of 1,4-diacetoxy-but-2-ene in a polar and non-basic aprotic solvent, selected from among the nitriles, bis(2-methoxy)but-2ene, bis(2-methoxyethyl) ether and methylene chloride, at 80° C. to 140° C. in the presence of a transition metal halide, and that, in the presence of an alcohol, the rates increase and are comparable to those determined for the carbonylation of but-2-ene-1,4-diol. With regard to this latter substrate, it is also indicated that it is not possible to achieve satisfactory yields of straight-chain carbonylation products under the aforementioned conditions and, in this context, preference is given to the substrates substituted in the 1,4-position by alkoxy groups.

Also in this regard, it would therefore appear that 1,4-diacetoxy-but-2-ene cannot be regarded as a promising substrate for forming dicarbonylated straight-chain products.

However, 1,4-diacetoxy-but-2-ene is readily available by acetoxylation of butadiene. It would therefore be highly desirable to provide a process enabling dicarbonylated straight-chain compounds to be prepared with a high efficiency from 1,4-diacetoxy-but-2-ene, for example, and more generally from butenes disubstituted by acyloxy groups.

SUMMARY OF THE INVENTION

Accordingly, a major object of the present invention is the provision of an improved process for the preparation of hexene-1,6-dioic acids by reacting carbon monoxide and water with at least one butene disubstituted by acyloxy groups, in the presence of a catalyst based on palladium and a quaternary onium chloride of a Group VB element selected from between nitrogen and phosphorus, such element being tetracoordinated at the carbon atoms and with the proviso that the nitrogen may be coordinated to two pentavalent phosphorus atoms.

DETAILED DESCRIPTION OF THE PREFERRED EMBODIMENTS OF THE INVENTION

More particularly according to the present invention, it has now surprisingly and unexpectedly been found that the subject process permits the dicarbonylation to be carried out under pressure and temperature conditions acceptable on an industrial scale, with an appreciable selectivity for the straight-chain dicarbonylated compound.

The process of the invention can be represented by the following reaction scheme, when the starting material is a but-2-ene disubstituted in the 1,4-position by acyloxy groups:

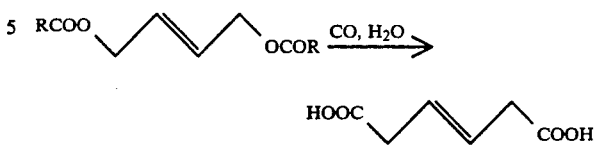

in which R is a straight-chain or branched alkyl radical having from 1 to 12 carbon atoms, optionally substituted by a phenyl group, or an aryl radical having 6 to 10 carbon atoms, optionally substituted by one or two alkyl radicals having from 1 to 4 carbon atoms; or substituted such radicals bearing 1 to 3 substitutents selected from among fluorine and chlorine atoms and dialkylamino and N,N-dialkylamido radicals, in which the alkyl moieties contain at most 4 carbon atoms.

The process according to the present invention requires the use of at least one butene disubstituted by acyloxy groups. By "acyloxy" groups are intended radicals of the formula RCOO— in which R is as defiend above; by "disubstituted butenes" are intended the compounds of but-2-ene substituted in the 1 and 4 positions and the compounds of but-1-ene substituted in the 3 and 4 positions. Of course, mixtures of but-2-ene disubstituted by acyloxy groups of different nature, mixture of but-1-ene disubstituted by acyloxy groups of different nature or mixtures of disubstituted but-2-ene and but-1-ene are also within the scope of the present invention.

Indeed, it has now been found that the selectivity for the straight-chain acid is substantially the same when a but-2-ene disubstituted by acyloxy groups in the 1,4-positions or a but-1-ene disubstituted by acyloxy groups in the 3 and 4 positions is used as the starting material.

The following are exemplary of butenes disubstituted by acyloxy groups: diacetoxybutenes, dipropionyloxybutenes, dibutyryloxybutenes and dibenzoyloxybutenes.

1,4-Diacetoxy-but-2-ene, 3,4-diacetoxy-but-1-ene, and mixtures thereof, are very particularly suitable for carrying out the present invention.

The process according to this invention also requires the presence of water.

The amount of water to be used in the present process is not critical and can vary over wide limits.

To advantageously carry out the reaction of the invention, the molar ratio of water to disubstituted butene will range from 1 to 100 and preferably from 1 to 50.

The process according to the present invention is carried out in the presence of a catalyst based on palladium.

Although the precise nature of the one or more catalytically active species in the reaction may not be totally elucidated, it has been found that diverse palladium compounds and metallic palladium are useful precursors for carrying out the process of the invention.

The following are representative sources of palladium which can be used for carrying out the process of the invention:

(i) metallic palladium, where appropriate deposited on a carrier, such as carbon, alumina or silica;

(ii) $PdCl_2$, $Pd(OAc)_2$, $PBu_4PdCl_3$ (Bu = n-butyl);

(iii) the salts or $\pi$-allyl complexes of palladium, in which the anion coordinated to the Pd cation is selected from among the following anions: carboxylates such as formate, acetate, propionate and benzoate; acetylacetonate and halides such as Cl⁻ and Br⁻, and preferably Cl⁻.

The precise amount of catalyst to be used, which can vary over wide limits, will above all depend on a compromise between the desired efficiency and the consumption of catalyst and on the other conditions selected for the reaction. In general, good results can be obtained with a palladium concentration in the reaction mixture ranging from $10^{-3}$ to 1 mol/l. Preferably, this concentration ranges from $2.10^{-3}$ to $5.10^{-2}$ mol/l.

One of the essential characteristics of the process of the invention is that the reaction is also carried out in the presence of a quaternary onium chloride of a Group VB element selected from between nitrogen and phosphorus, such element being tetracoordinated to the carbon atoms and with the proviso that the nitrogen may be coordinated to two pentavalent phosphorus atoms.

By "quaternary onium cations in which the Group VB element is tetracoordinated to the carbon atoms" are intended cations formed from nitrogen or phosphorus and four monovalent, identical or different, hydrocarbon groups, in which the free valency is borne by a carbon atom, each group being bonded to the above element by the said free valency and any two of these groups, moreover, being able to form together a divalent radical.

To advantageously carry out the process of the invention, the quaternary onium chloride has a quaternary onium cation corresponding to one of the formulae (I) to (IV) below:

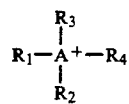   (I)

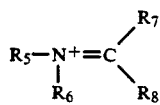   (II)

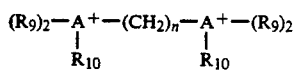   (III)

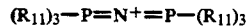   (IV)

in which formulae A is nitrogen or phosphorus; $R_1$, $R_2$, $R_3$ and $R_4$, which may be identical or different, are each a straight-chain or branched alkyl radical having from 1 to 16 carbon atoms, optionally substituted by a phenyl, hydroxyl, halogeno, nitro, alkoxy or alkoxycarbonyl group; a straight-chain or branched alkenyl radical having from 2 to 12 carbon atoms, preferably 4 to 8 carbon atoms; an aryl radical having 6 to 10 carbon atoms, optionally substituted by one or more alkyl radicals having from 1 to 4 carbon atoms, alkoxy, alkoxycarbonyl or halogeno; with the proviso that two of said radicals $R_1$ to $R_4$ may together form a straight-chain or branched alkylene, alkenylene or alkadienylene radical having from 3 to 6 carbon atoms; $R_5$, $R_6$, $R_7$ and $R_8$, which may be identical or different, are each a straight-chain or branched alkyl radical having from 1 to 4 carbon atoms; with the proviso that the radicals $R_7$ and $R_8$ may together form an alkylene radical having from 3 to 6 carbon atoms; and with the further proviso that the radicals $R_6$ and $R_7$ or $R_6$ and $R_8$ may together form an alkylene, alkenylene or alkadienylene radical having 4 carbon atoms and forming, with the N atom, a nitrogen-containing heterocyclic radical; $R_9$ is a straight-chain or branched alkyl radical having from 1 to 4 carbon atoms or a phenyl radical; $R_{10}$ is a straight-chain or branched alkyl radical having from 1 to 4 carbon atoms, identical to or different from $R_9$; a straight-chain or branched alkenyl radical having from 2 to 12 carbon atoms, preferably 4 to 8 carbon atoms; n is an integer greater than or equal to 1 and less than or equal to 10 and preferably less than or equal to 6; and $R_{11}$ is an aryl radical having 6 to 10 carbon atoms, optionally substituted by one or more alkyl groups having from 1 to 4 carbon atoms, alkoxy, alkoxycarbonyl or halogeno.

The following cations are exemplary of quaternary onium cations corresponding to formula (I):
Tetramethylammonium;
Triethylmethylammonium;
Tributylmethylammonium;
Trimethyl(n-propyl)ammonium;
Tetraethylammonium;
Tetrabutylammonium;
Dodecyltrimethylammonium;
Methyltrioctylammonium;
Heptyltributylammonium;
Tetrapropylammonium;
Tetrapentylammonium;
Tetrahexylammonium;
Tetraheptylammonium;
Tetraoctylammonium;
Tetradecylammonium;
Butyltripropylammonium;
Methyltributylammonium;
Pentyltributylammonium;
Methyldiethylpropylammonium;
Ethyldimethylpropylammonium;
Tetradodecylammonium;
Tetraoctadecylammonium;
Hexadecyltrimethylammonium;
Benzyltrimethylammonium;
Benzyldimethylpropylammonium;
Benzyldimethyloctylammonium;
Benzyltributylammonium;
Benzyltriethylammonium;
Phenyltrimethylammonium;
Benzyldimethyltetradecylammonium;
Benzyldimethylhexadecylammonium;
Dimethyldiphenylammonium;
Methyltriphenylammonium;
But-2-enyltriethylammonium;
N,N-Dimethyl-tetramethyleneammonium;
N,N-Diethyl-tetramethyleneammonium;
Tetramethylphosphonium;
Tetrabutylphosphonium;
Ethyltrimethylphosphonium;
Trimethylpentylphosphonium;
Octyltrimethylphosphonium;
Dodecyltrimethylphosphonium;
Trimethylphenylphosphonium;
Diethyldimethylphosphonium;
Dicyclohexyldimethylphosphonium;
Dimethyldiphenylphosphonium;
Cyclohexyltrimethylphosphonium;
Triethylmethylphosphonium;
Methyl-tri(isopropyl)phosphonium;
Methyl-tri(n-propyl)phosphonium;
Methyl-tri(n-butyl)phosphonium;

Methyl-tri(2-methylpropyl)phosphonium;
Methyltricyclohexylphosphonium;
Methyltriphenylphosphonium;
Methyltribenzylphosphonium;
Methyl-tri(4-methylphenyl)phosphonium;
Methyltrixylylphosphonium;
Diethylmethylphenylphosphonium;
Dibenzylmethylphenylphosphonium;
Ethyltriphenylphosphonium;
Tetraethylphosphonium;
Ethyl-tri(n-propyl)phosphonium;
Triethylpentylphosphonium;
Hexadecyltributylphosphonium;
Ethyltributylphosphonium;
N-butyl-tri(n-propyl)phosphonium;
Butyltriphenylphosphonium;
Benzyltriphenylphosphonium;
(β-Phenylethyl)dimethylphenylphosphonium;
Tetraphenylphosphonium;
Triphenyl(4-methylphenyl)phosphonium;
Tetrakis(hydroxymethyl)phosphonium;
Tetrakis(2-hydroxyethyl)phosphonium.

The following cations are exemplary of the cations corresponding to formula (II):
N-methylpyridinium;
N-ethylpyridinium;
N-hexadecylpyridinium;
N-methylpicolinium.

The following cations are exemplary of the cations corresponding to formula (III):
1,2-Bis(trimethylammonium)ethane;
1,3-Bis(trimethylammonium)propane;
1,4-Bis(trimethylammonium)butane;
1,3-Bis(trimethylammonium)butane;

And the following cations are exemplary of the cations corresponding to formula (IV):
Bis(triphenylphosphine)iminium;
Bis(tritolylphosphine)iminium.

Advantageously, the cations used are those onium cations corresponding to formula (I) above, in which:

A represents phosphorus; and $R_1$, $R_2$, $R_3$ and $R_4$, which may be identical or different, are each a straight-chain or branched alkyl radical having from 1 to 8 carbon atoms or a phenyl or 4-methylphenyl radical.

A tetraalkylphosphonium chloride is preferably used.

Tetrabutylphosphonium chloride, which is readily available and particularly efficient, is very particularly preferred.

It will be appreciated that certain palladium compounds, such as $PBu_4PdCl_3$, which has been mentioned above and results from the reaction between equivalent molar amounts of $PBu_4Cl$ and $PdCl_2$, can at one and the same time constitute a source of palladium and a means for providing a quaternary onium chloride as indicated above.

It has been found that the beneficial effect afforded by the presence in the carbonylation mixture of a quaternary onium chloride corresponding to the above definition is perceptible from an onset onium cation/palladium molar ratio of 0.5; particularly desirable results are obtained when said ratio ranges from 1 to 50, and it is even possible to select a higher ratio without prejudice to the reaction. In fact, the quaternary onium chloride can be used in a relatively significant amount and, accordingly, also serves as a diluent for the reaction mixture.

It will generally be possible to carry out the reaction in liquid phase at a temperature ranging from 50 to 150° C., preferably from 80° to 130° C., under a carbon monoxide pressure ranging from 10 to 250 bar (1,000 to 25,000 KPa), preferably from 15 to 180 bar (1,500 and 18,000 KPa).

Inert gases, such as nitrogen, argon or carbon dioxide, can be present with the carbon monoxide.

Of course, the reaction can be carried out in the presence of solvents or diluents exogenous to the reaction mixture, such as aromatic hydrocarbons, esters, ketones, nitriles or carboxylic acid amides.

In a preferred embodiment of the process according to the present invention, the reaction is carried out in N-methylpyrrolidone.

The concentration of disubstituted butene can also vary over wide limits.

Upon completion of the reaction or of the desired reaction time, the desired diacid is recovered by any appropriate means, for example by extraction.

In order to further illustrate the present invention and the advantages thereof, the following specific examples are given, it being understood that same are intended only as illustrative and in nowise limitative.

In said examples to follow, the degree of conversion was 100% and the formation of the following various acids was observed:

HD: mixture of hex-3-enedioic and hex-2-enedioic acids, in which hex-3-enedioic acid was the predominant;

Ac.$C_5$: mixture of valeric, 2-methylbutyric, pent-3-enoic, pent-2-enoic and pent-4-enoic acids, in which pent-3-enoic acid was the predominant.

$C_6$sat.: mixture of ethylsuccinic, methylglutaric and adipic acids, in which methylglutaric acid was the predominant;

PDO: pentadienoic acid, the number of moles formed per 100 moles of diacetoxybutene charged being indicated for each group.

EXAMPLES 1 TO 11:

The following materials were introduced into a 125 cm³ stainless steel (Hastelloy B2) autoclave previously purged with argon:

(i) 8.6 g (50 mmol) of 1,4-diacetoxy-but-2-ene;

(ii) 1.8 g (100 mmol) of water;

(iii) 1 mg-at. of palladium in the form indicated in Table I below;

(iv) 5 g (17 mmol) of $PBu_4Cl$;

(v) 25 cm³ of solvent, the nature of which is indicated in Table I below.

The autoclave was hermetically sealed, placed in an agitated furnace and adjusted for introduction of gas under pressure. The reactor was purged cold with carbon monoxide and brought to 100° C. The pressure was then adjusted to 120 bar. After a reaction time of 6 hours (unless indicated otherwise), the autoclave was cooled and degassed.

The resultant reaction mixture was diluted to 100 cm³ with the solvent.

An aliquot portion was esterified with methanol and then analyzed by gas phase chromatography.

TABLE I

| Example No. | Pd | Solvent | t(h) | HD | Ac.C$_5$ | C$_6$sat. | PDO |
|---|---|---|---|---|---|---|---|
| 1 | PdCl | CH$_3$CN | | 34 | 35 | 17 | 0 |
| (a) | PdCl | CH$_3$CN | | 6 | 16 | 5 | 4 |
| (b) | PdCl | CH$_3$CN | | 2 | 33 | 11 | 1 |
| 2 | Pd(OAc)$_2$ | CH$_3$CN | 2 | 38 | 2 | 1 | 15 |
| 3* | id + HBF$_4$ | CH$_3$CN | | 22 | 32 | 17 | 0 |
| 4 | PdCl$_2$ | NMP | 3 | 68 | 2 | 0 | 12 |
| 5 | Pd(OAc)$_2$ | NMP | | 22 | 1 | 0 | 41 |
| 6 | Pd(dba)$_2$ | NMP | | 20 | 0.5 | 0 | 40 |
| 7 | MePO$_3$PdCl$_3$ | NMP | | 60 | 1 | 0 | 12 |
| 8* | Pd/C | NMP | | 17 | 3 | — | 54 |
| 9 | PdCl$_2$ | PBu$_4$Cl | 3 | 80 | 4 | 1 | 1 |
| 10 | PdCl$_2$ | DMF | | 33 | 0 | 0 | 11 |
| 11 | PdCl$_2$ | Sulfolane | | 38 | 20 | 0 | 0.5 |

(a): PBu$_4$Cl absent
(b): PBu$_4$Cl replaced by PBu$_4$Br
3* catalyst: Pd(OAc)$_2$ + 2 mmol HBF$_4$
8* catalyst: Pd/C (10% palladium); 1 mmol Pd
t(h): absorption time if it was less than 6 hours

EXAMPLE 12

The procedure of Example 4 was repeated, using only 0.5 mg-at. of palladium in the form of PdCl$_2$. The following results were obtained after a reaction time of 12 hours.
(a) HD: 80%
(b) Ac.C$_5$: 0.5%
(c) C$_6$sat.: 0%
(d) PDO: 14%

EXAMPLE 13

The procedure of Example 4 was repeated, using only 0.25 mg-at. of palladium in the form of PdCl$_2$. The following results were obtained after a reaction time of 12 hours:
(a) HD: 65%
(b) Ac.C$_5$: 2%
(c) C$_6$sat.: 0%
(d) PDO: 12%

EXAMPLES 14 AND 15

The procedure of Example 4 was repeated, using, respectively, 2.5 g and 15 g of PBu$_4$Cl and adjusting the volume of N-methylpyrrolidone for each experiment in such manner that the total volume of the charge was constant.

The results obtained are reported in Table II below, in which the results and particular conditions of Examples 4 and 9 above are duplicated.

TABLE II

| Example No. | PBu$_4$Cl(g) | t(h) | HD | Ac.C$_5$ | C$_6$sat. | PDO |
|---|---|---|---|---|---|---|
| 14 | 2.5 | 6 | 55 | 1 | 0 | 13 |
| 4 | 5 | 3 | 68 | 2 | 0 | 12 |
| 15 | 15 | 3 | 80 | 3 | 0 | 3 |
| 9 | 30 | 3 | 78 | 4 | 1 | 1 |

EXAMPLE 16

The procedure of Example 4 was repeated, replacing the 1,4-diacetoxy-but-2-ene in the charge by an equivalent amount of 1,2-diacetoxy-but-3-ene.

After a reaction time of 6 hours, the results obtained were as follows:
(a) HD: 65%
(b) Ac.C$_5$: 1%
(c) C$_6$sat.: 0%
(d) PDO: 10%

EXAMPLE 17

The procedure of Example 4 was repeated, at 130° C. After a reaction time of 3 hours, the results obtained were as follows
(a) HD: 45%
(b) Ac.C$_5$: 7%
(c) C$_6$sat.: 0%
(d) PDO: 0%

EXAMPLE 18

The procedure of Example 4 was repeated, at 70° C. After a reaction time of 6 hours, the results obtained were as follows:
(a) HD: 30%
(b) Ac.C$_5$: 2%
(c) C$_6$sat.: 0%
(d) PDO: 33%

EXAMPLE 19

The procedure of Example 4 was repeated, under a pressure of 180 bars.
Approximately the same results were obtained.

EXAMPLE 20

The procedure of Example 4 was repeated, under a pressure of 15 bars.
After a reaction time of 6 hours, the results obtained were as follows:
(a) HD: 40%
(b) Ac.C$_5$: 30%
(c) C$_6$sat.: 0%
(d) PDO 0%

EXAMPLE 21

The procedure of Example 4 was repeated, under a pressure of 60 bars.
After a reaction time of 6 hours, the results obtained were as follows:
(a) HD: 75%
(b) Ac.C$_5$: 3%
(c) C$_6$sat.: 0%
(d) PDO: 9%

EXAMPLES 22 TO 24

The procedure of Example 4 was repeated twice, using, respectively, 25 mmol and 100 mmol of 1,4- diacetoxy-but-2-ene (DAB), in each experiment maintaining a 1,4-diacetoxy-but-2-ene/H₂O molar ratio of ½ and maintaining the volume of the charge constant by adjusting the amount of NMP (Examples 22 and 23).

The procedure of Example 1 was repeated, using 25 mmol of 1,4-diacetoxy-but-2-ene, maintaining the molar ratio of the latter with water at ½ and maintaining the volume of the charge constant by adjusting the amount of CH₃CN (Example 24).

The results obtained are reported in Table III below:

TABLE III

| Example No. | Solvent | DAB mmol | t(h) | Results (%) | | | |
|---|---|---|---|---|---|---|---|
| | | | | HD | Ac.C₅ | C₆sat. | PDO |
| 22 | NMP | 25 | 3 | 80 | 1 | ? | 7 |
| 4 | NMP | 50 | 3 | 68 | 2 | 0 | 12 |
| 23 | NMP | 100 | | 60 | 2 | 0 | 15 |
| 24 | CH₃CN | 25 | | 68 | 23 | 22 | 0 |
| 1 | CH₃CN | 50 | | 45 | 35 | 17 | 0 | t(h): absorption time if it was less than 6 hours

EXAMPLES 25 AND 26

The procedure of Example 1 was repeated, varying the amount of water charged.

The particular conditions and the results obtained are reported in Table IV below:

TABLE IV

| Example No. | H₂O mmol | t(h) | Results (%) | | | |
|---|---|---|---|---|---|---|
| | | | HD | Ac.C₅ | C₆sat. | PDO |
| 1 | 100 | 6 | 45 | 35 | 17 | 0 |
| 25 | 200 | 2.5 | 48 | 27 | 9 | 0 |
| 26 | 500 | 3 | 45 | 4 | 5 | 5 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a hexene-1,6-dioic acid, comprising reacting carbon monoxide and water with at least one butene disubstituted by acyloxy groups, in the presence of a catalytically effective amount of palladium and at least one quaternary onium chloride of one of the Group VB elements nitrogen or phosphorus, such element being tetracoordinated via carbon atoms and with the proviso that such nitrogen atom may be coordinated to two pentavalent phosphorus atoms.

2. The process as defined by claim 1, said quaternary onium chloride of nitrogen or phosphorus comprising a quaternary onium cation having one of the formulae (I) to (IV) below:

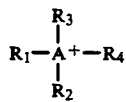
(I)

in which formulae A is nitrogen or phosphorus; $R_1$, $R_2$, $R_3$ and $R_4$, which may be identical or different are each a straight-chain or branched alkyl radical having from 1 to 16 carbon atoms, substituted or unsubstituted by a phenyl, hydroxyl, halogeno, nitro, alkoxy or alkoxycarbonyl substituent; a straight-chain or branched alkenyl radical having from 2 to 12 carbon atoms; an aryl radical having 6 to 10 carbon atoms, substituted or unsubstituted by one or more alkyl radicals having from 1 to 4 carbon atoms, or alkoxy, alkoxycarbonyl or halogeno substituents; with the proviso that two of said radicals $R_1$ to $R_4$ may together form a straight-chain or branched alkylene, alkenylene or alkadienylene radical having from 3 to 6 carbon atoms; $R_5$, $R_6$, $R_7$ and $R_8$, which may be identical or different, are each a straight-chain or branched alkyl radical having from 1 to 4 carbon atoms; with the proviso that the radicals $R_7$ and $R_8$ may together form an alkylene radical having from 3 to 6 carbon atoms; and with the further proviso that the radicals $R_6$ and $R_7$ or $R_6$ and $R_8$ may together form an alkylene, alkenylene or alkadienylene radical having 4 carbon atoms and forming, with the N atom, a nitrogen-containing heterocyclic radical; $R_9$ is a straight-chain or branched alkyl radical having from 1 to 4 carbon atoms or a phenyl radical; $R_{10}$ is a straight-chain or branched alkyl radical having from 1 to 4 carbon atoms, identical to or different from $R_9$; or a straight-chain or branched alkenyl radical having from 2 to 12 carbon atoms; n is an integer greater than or equal to 1 and less than or equal to 10; and $R_{11}$ is an aryl radical having 6 to 10 carbon atoms, substituted or unsubstituted by one or more alkyl groups having from 1 to 4 carbon atoms, or alkoxy, alkoxycarbonyl or halogeno substituents.

3. The process as defined by claim 2, said quaternary onium cation having the formula (I), in which A is phosphorus, and $R_1$, $R_2$, $R_3$ and $R_4$, which may be identical or different, are each a straight-chain or branched alkyl radical having from 1 to 8 carbon atoms, or a phenyl or 4-methylphenyl radical.

4. The process as defined by claim 1, said quaternary onium chloride comprising tetrabutylphosphonium chloride.

5. The process as defined by claim 1, wherein the molar ratio of the onium cation to palladium is greater than or equal to 1.

6. The process as defined by claim 1, wherein the concentration of palladium in the reaction mixture ranges from $10^{-3}$ to 1 mol/l.

7. The process as defined by claim 1, wherein the molar ratio of water to disubstituted butene ranges from 1 to 100.

8. The process as defined by claim 1, carried out at a reaction temperature ranging from 50° to 150° C.

9. The process as defined by claim 1, carried out at a pressure ranging from 10 to 250 bar.

10. The process as defined by claim 1, said disubstituted butene comprising 1,4-diacetoxy-but-2-ene, 3,4-diacetoxy-but-1-ene, or admixture thereof.

11. The process as defined by claim 1, carried out in the presence of an organic solvent or diluent.

12. The process as defined by claim 11, carried out in an N-methylpyrrolidone solvent.

13. The process as defined by claim 7, said molar ratio ranging from 1 to 50.

14. The process as defined by claim 8, said reaction temperature ranging from 80° to 130° C.

15. The process as defined by claim 9, said pressure ranging from 15 to 180 bar.

16. The process as defined by claim 2, said quaternary onium cation having the formula (II).

17. The process as defined by claim 2, said quaternary onium cation having the formula (III).

18. The process as defined by claim 2, said quaternary onium cation having the formula (IV).

* * * * *